United States Patent
Matsumoto et al.

[11] Patent Number: 5,803,900
[45] Date of Patent: Sep. 8, 1998

[54] LIGHT SOURCE DEVICE FOR ENDOSCOPE PROVIDED WITH NONCIRCULAR OPENING

[75] Inventors: Seiji Matsumoto, Omiya; Etsuo Nakano; Suwao Satoh, both of Okaya, all of Japan

[73] Assignee: Fuji Photo Optical Co., Ltd., Omiya, Japan

[21] Appl. No.: 984,021

[22] Filed: Dec. 3, 1997

[30] Foreign Application Priority Data

Dec. 9, 1996 [JP] Japan .................................. 8-346752

[51] Int. Cl.$^6$ ........................................ A61B 1/04
[52] U.S. Cl. ............................ 600/181; 600/180; 348/68; 348/363; 348/367
[58] Field of Search ...................... 600/178, 180, 600/181; 348/68, 363, 362, 367, 368

[56] References Cited

U.S. PATENT DOCUMENTS

| | | | |
|---|---|---|---|
| 4,072,147 | 2/1978 | Hett | 600/181 |
| 4,425,599 | 1/1984 | Rieder et al. | 600/181 |
| 4,704,520 | 11/1987 | Kanno et al. | 600/180 |
| 4,803,550 | 2/1989 | Yabe et al. | 600/180 |
| 4,928,172 | 5/1990 | Uehara et al. | 600/180 |
| 4,967,269 | 10/1990 | Sasagawa et al. | 600/180 |
| 5,642,456 | 6/1997 | Baker et al. | 600/180 |

*Primary Examiner*—Gene Mancene
*Assistant Examiner*—Ira Hatton
*Attorney, Agent, or Firm*—Ronald R. Snider

[57] ABSTRACT

A light source device for an endoscope provided with a noncircular opening which is capable of stabilizing the rate of change of the quantity of illuminating light with the quantity of movement of the stop blade and thereby preventing the hunting phenomenon of the stop blade in close-up or the like. The device comprises: a gate portion with a noncircular opening for linearly changing the quantity of light from the light source formed therein; a stop blade for controlling the quantity of light passing through the noncircular opening of the gate portion; and a motor for driving the stop blade. The noncircular opening has two V-shaped portions having different opening angles. The stop blade is provided with a circular auxiliary opening for passing part of the light therethrough. Owing to the V-shaped portions and the auxiliary opening, a change of the quantity of output light with the amount of movement of the stop blade is made linear and the hunting phenomenon of the stop blade is prevented even in the region where the quantity of light is regulated to a small quantity.

2 Claims, 4 Drawing Sheets

LIGHT SOURCE DEVICE FOR ENDOSCOPE PROVIDED WITH NONCIRCULAR OPENING

BACKGROUND OF THE INVENTION

This application claims the priority of Japanese Patent Applications No. 8-346752 filed on Dec. 9, 1996 which is incorporated herein by reference.

1. Field of the Invention

The present invention relates to a light source device for an endoscope provided with a noncircular opening and, more particularly, to a light source device for an endoscope for medical or industrial use which is capable of automatic light control.

2. Description of the Related Art

An endoscope for medical or industrial use is provided with a light source device for illuminating the interior of the body as an object of observation, and an ALC (automatic light control) function is essential to the light source device used for an endoscope.

FIG. 7 shows the stop portion of the automatic light control means. As shown in FIG. 7, the stop portion is composed of a gate portion 2 having a circular opening 1 for passing the light from the light source therethrough, a stop blade 3 for controlling the aperture area of the opening 1, and a motor 4 for driving the stop blade 3. The motor 4 is controlled by an ALC circuit (not shown).

The ALC circuit inputs a part of the video signals of the object of observation which are processed by a processor circuit so as to form an image, and forms an iris control signal on the basis of the input video signals. The motor 4 is driven under the control of the ALC circuit, so that the stop blade 3 is driven and the aperture area of the circular opening 1 is controlled. By the control of the aperture area, the quantity of output light (iris level) is adjusted to an appropriate value which enables the object of observation to be constantly illuminated with appropriate brightness.

In a conventional light source device, however, since the opening 1 of the gate portion 2 is made circular for passing the light from the light source therethrough, and the light shading end of the stop blade 3 for varying the aperture area is made linear, the quantity of output light suddenly changes especially in the region where the aperture area of the opening 1 is made small. In close-up, the stop blade 3 is sometimes moved to such a great extent that only a slight portion of the opening 1 in the vicinity of the periphery is open. In such a state, the rate of change of the quantity of illuminating light with the amount of movement of the stop blade 3 becomes disadvantageously very large.

FIG. 8 is a graph of a change of the quantity of illuminating light with the amount of movement of the stop blade 3 in a conventional device. As shown in FIG. 8, in the region of a small light quantity, there is a portion P in which a change of the quantity of light becomes large with a small amount of movement of the stop blade 3. In such a portion P, the stopping operation is unstable and the hunting phenomenon of the stop blade 3 is apt to be produced. That is, the stop blade 3 unfavorably repeats vibration.

SUMMARY OF THE INVENTION

Accordingly, it is an object of the present invention to eliminate the above-described problem in the related art and to provide a light source device for an endoscope provided with a noncircular opening which is capable of stabilizing the rate of change of the quantity of illuminating light with the amount of movement of a stop blade and preventing the hunting phenomenon of the stop blade in close-up or the like.

To achieve this end, in one aspect of the present invention, there is provided a light source device for an endoscope comprising: a gate portion including a noncircular opening for passing the light from a light source therethrough and linearly changing the quantity of light from the light source; a stop blade for controlling the quantity of light passing through the noncircular opening of the gate portion; and a driving member for driving the stop blade.

The noncircular opening may have a V shape.

It is possible to adopt an opening, for example, having a fan shape with a V-shaped lower end as the noncircular opening, and a stop blade may be moved from the upper side to the lower side of the noncircular opening. According to this structure, even in the region of a small quantity of light, a change of the quantity of light with the amount of movement of the stop blade becomes linear, and a sudden change is prevented. Stable illumination free from the hunting phenomenon of the stop blade is thus possible even close-up.

In a light source device for an endoscope provided in another aspect of the present invention, the stop blade is a single blade with an auxiliary opening for passing part of light therethrough formed therein and the auxiliary opening is moved to the noncircular portion of the noncircular opening.

For example, a small hole having an appropriate size is provided as the auxiliary opening. In this case, when the small hole passes the V-shaped portion, it is also possible to gently and linearly change the quantity of output light, so that stabler control of the quantity of light is enabled. In addition, the auxiliary opening also has a role of compensating for the lack of quantity of light which is set by the noncircular opening.

DESCRIPTION OF THE PREFERRED EMBODIMENT

Figure 1:
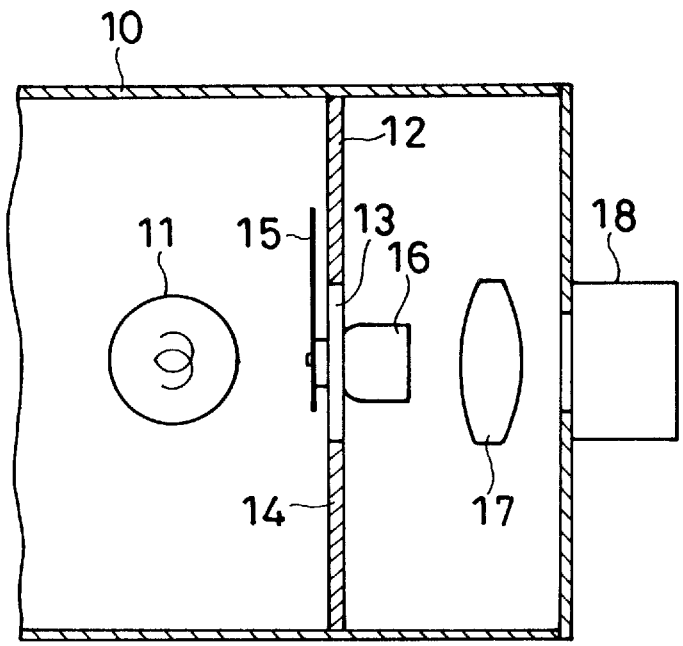
FIG. 1 is a side elevational view of the internal structure of an embodiment of a light source device for an endoscope provided with a noncircular opening according to the present invention.
Figure 2:
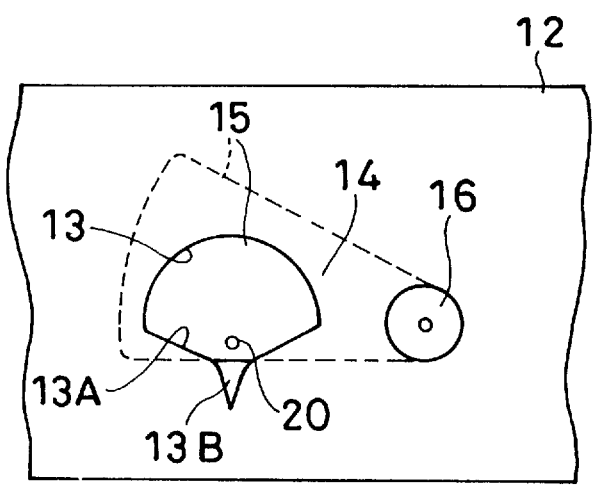
FIG. 2 shows the structure of the stop portion of the embodiment shown in FIG. 1.
Figure 3:
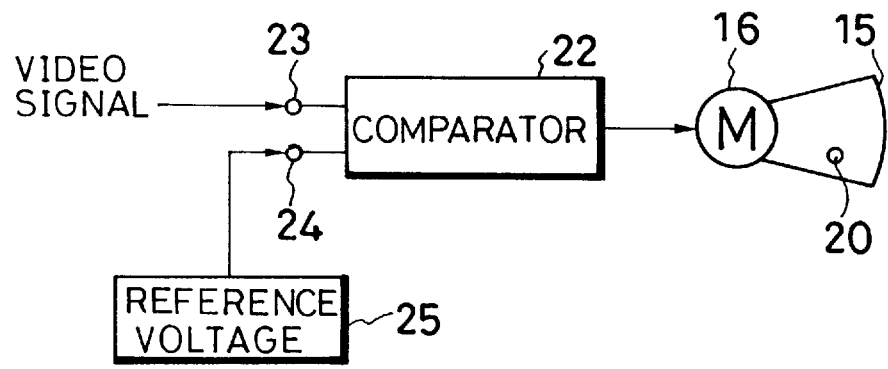
FIG. 3 is a block diagram of the circuit structure for controlling the quantity of light in the embodiment shown in FIG. 1.

FIG. 1 shows the internal structure of an embodiment of a light source device for an endoscope according to the present invention seen from the side surface side, FIG. 2 shows the structure of the stop portion of the embodiment, and FIG. 3 shows the circuit structure for controlling the quantity of light in the embodiment. In FIG. 1, a light source lamp 11 is disposed in the light source device 10, and a diaphragm 12 is disposed in front of the light source lamp 11. A gate portion 14 with a noncircular opening 13 formed therein is integrally provided with the diaphragm 12.

A single stop blade 15 for changing the aperture area of the noncircular opening 13 is provided on the gate portion 14. The stop blade 15 is driven by a motor 16. A light guide connector receiver 18 is disposed in front of the noncircular opening 13 via a condenser lens 17. The light guide connector of an electron endoscope is to be connected to the connector receiver 18.

FIG. 2 shows the shape of the noncircular opening 13. As shown in FIG. 2, the noncircular opening 13 has a fan shape as a whole, and has two V-shaped portions 13A and 13B each of which has a width gradually reducing toward the lower end. In the V-shaped portions 13A and 13B, the opening angles are different from each other. The stop blade 15 is disposed at the position which enables the stop blade 15 to vary the aperture area of the noncircular opening 13 by moving vertically while rotating around the shaft of the motor 16. Owing to the V-shaped portions 13A and 13B, it is possible to make a change of the aperture area linearly and gentle even in the region where the quantity of light is regulated to a small quantity.

Figures 4A, 4B:
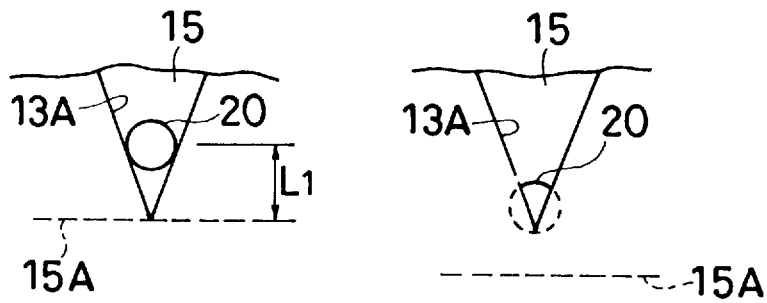
FIGS. 4(A) to 4(C) show the operation of the auxiliary opening in the V-shaped portion in the embodiment shown in FIG. 1.

The stop blade 15 is provided with a small auxiliary opening 20 at the position which passes the lower end of the V-shaped portion 13B. To state this more concretely, the auxiliary opening 20 is formed at the position L1 distant from the lower end 15A of the stop blade 15 so that the right and left edges of the auxiliary opening 20 may come into contact with the straight lines of the V-shaped portion 13B when the lower end 15A of the stop blade 15 is located at the lower end of the V-shaped portion 13B, as shown in FIG. 4(A). Owing to the auxiliary opening 20, when the lower end 15A of the stop blade 15 is moved below the lower end of the V-shaped portion 13B, it is possible to not only linearly change the quantity of output light but also increase the quantity of light output from the light source lamp 11.

In FIG. 3, a comparator 22 is connected to the motor 16 which drives the stop blade 15. A part (a predetermined voltage such as a luminance signal) of the video signals is input to one input terminal 23 of the comparator 22, and a reference voltage equivalent to the appropriate luminance level of the video signals is input to the other terminal from a reference voltage source 25. The comparator 22 compares the predetermined voltage of the video signals with the reference voltage thereof, and when the predetermined voltage is higher than the reference voltage, the comparator 22 instructs the motor 16 to rotate the stop blade 15 in the direction in which the quantity of output light is reduced. On the other hand, when the predetermined voltage is lower than the reference voltage, the comparator 22 instructs the motor 16 to rotate the stop blade 15 in the direction in which the quantity of output light is increased. When the predetermined voltage is equal to the reference voltage, the comparator 22 instructs the motor 16 to stop.

The operation of the embodiment having the above-described structure will now be explained. The light source lamp 11 outputs light from the noncircular opening 13, and the quantity of output light varies by the position to which the stop blade 15 is rotated. The stop blade 15 is rotated by the motor 16 which is driven in accordance with the output control signal from the comparator 22, as shown in FIG. 3. Since the comparator 22 compares the predetermined voltage which shows the luminance of the video signals with the reference voltage which shows the appropriate luminance level of the video signals, and when the luminance of the video signals is high, the comparator 22 instructs the motor 16 to rotate the stop blade 15 to the lower side, the quantity of output light is reduced. On the other hand, when the luminance is low, the comparator 22 instructs the motor 16 to rotate the stop blade 15 upward, so that the quantity of output light is increased. When the luminance is at the appropriate level, the stop blade 15 is stopped.

In this control of the quantity of light, when the close-up of an object of observation is taken, the controlling operation is executed in the region in which the quantity of light is regulated to a small quantity and the opening 13 is approximately closed, as shown in FIG. 2. Especially, in such a region, the quantity of output light is so controlled by the V-shaped portions 13A, 13B and the auxiliary opening 20 that a change in the quantity of output light is linear.

Figure 5:
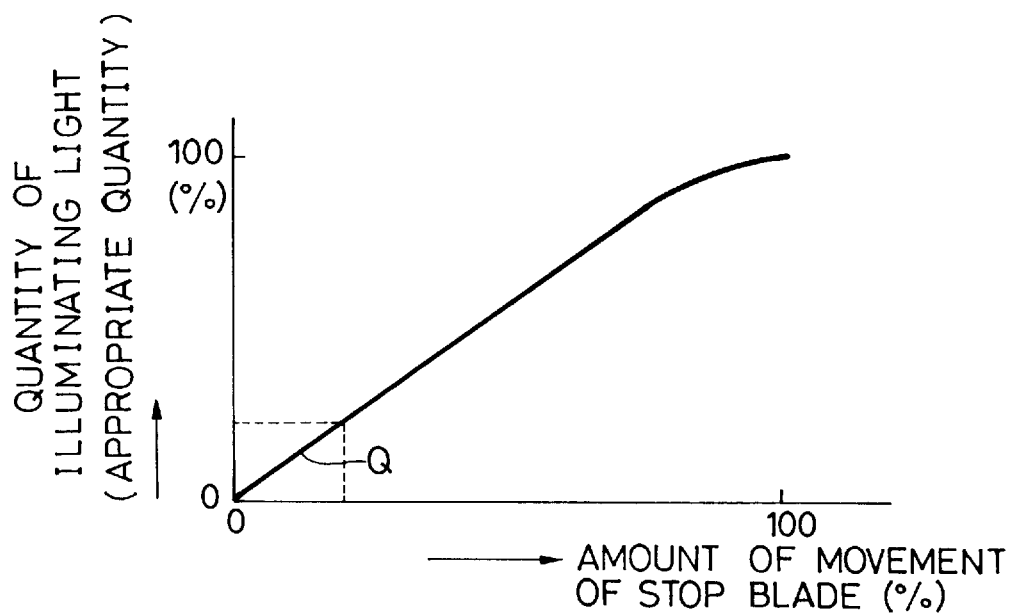
FIG. 5 is a graph of a change of the quantity of illuminating light with the amount of movement of the stop blade in the embodiment shown in FIG. 1.
Figure 7:
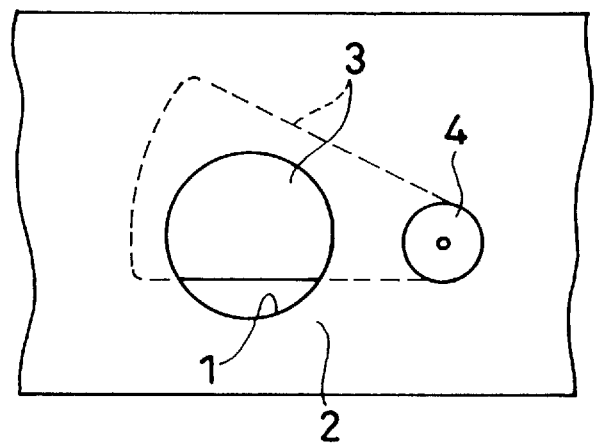
FIG. 7 shows the structure of the stop portion in a conventional light source device for an endoscope.
Figure 8:
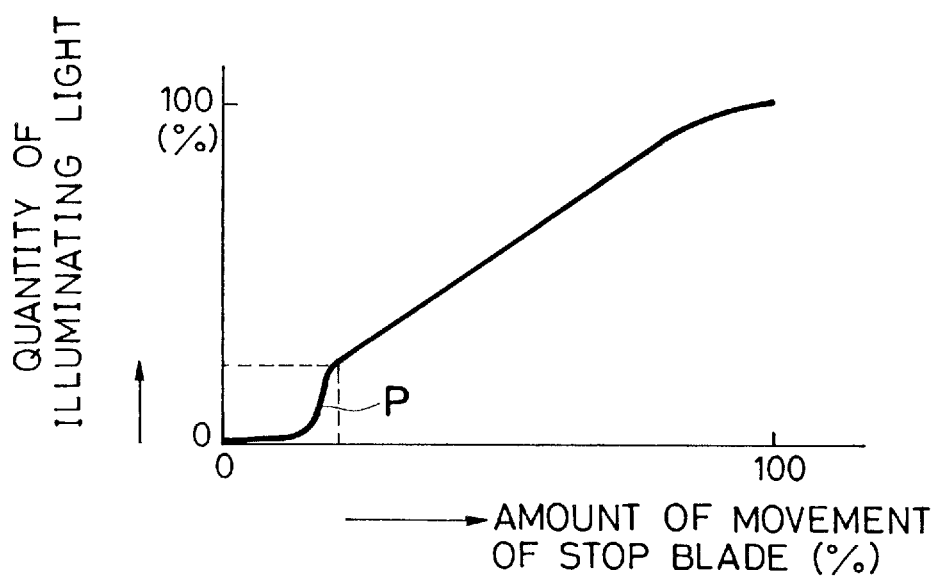
FIG. 8 is a graph of a change of the quantity of illuminating light with the amount of movement of the stop blade in the light source device shown in FIG. 7.

FIG. 5 is a graph of a change of the quantity of illuminating light (output light) with the amount of movement of the stop blade 15. As represented by a portion Q in FIG. 5, even in the region in which the aperture area of the opening 13 is regulated to a small area, the quantity of light linearly and gently changes owing to the V-shaped portions 13A, 13B and the auxiliary opening 20. It is therefore possible to prevent a sudden change (the portion P in FIG. 7) in the quantity of light as in the case of a conventional circular opening, and secure a stable stopping operation free from the hunting phenomenon of the stop blade 15.

In the noncircular opening 13, since the opening angles of the V-shaped portions 13A and 13B are different from each other, it is possible to reduce the loss of the quantity of output light as much as possible which is supposed to be caused when the aperture area of the noncircular opening 13 is large to some extent. More specifically, the smaller the opening angle of the V-shaped portion (13A, 13B), the gentler a change of the quantity of light with the amount of movement of the stop blade 15. However, when the aperture area of the noncircular opening 13 is not regulated to a small area, there is a loss in the quantity of passing light as compared with the case of a circular opening. On the other hand, in the region in which the stop blade 15 is located at a slightly upper position than the appropriate aperture opening and a change of the quantity of light with the amount of movement of the stop blade 15 is naturally gentle, the opening angle of the V-shaped portion may be large.

Accordingly, in the noncircular opening 13 in the embodiment, the V-shaped portion 13A having a large opening angle is provided below the arc portion, and the V-shaped portion 13B having a smaller opening angle is connected to the V-shaped portion 13A with curved lines. In this manner, the loss of the quantity of output light when the aperture area of the noncircular opening 13 is not regulated to a small area is made as small as possible.

Figure 4C:
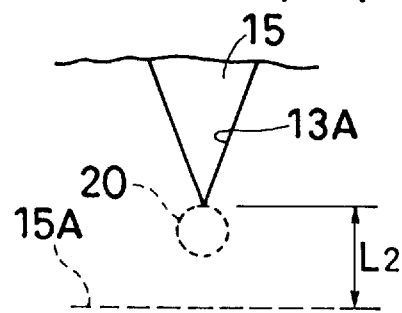

The auxiliary opening 20 in the stop blade 15 enables stabler control and it is capable of compensating for the lack of the quantity of light. FIGS. 4(A) to 4(C) show the operation of the auxiliary opening 20. As shown in FIG. 4(A), when the lower end 15A is located at the lower end of the V-shaped portion 13B, the right and left edges of the auxiliary opening 20 come into contact with the straight lines of the V-shaped portion 13B, so that only the light which passes through the auxiliary opening 20 is output.

When the stop blade 15 is rotated to the lower side from the position shown in FIG. 4(A), the aperture area of the auxiliary opening 20 is gradually regulated from both sides to a smaller area by the V-shaped portion 13B, as shown in FIG. 4(B), so that the quantity of output light is gently reduced. At the point of time where the lower end 15A of the stop blade 15 is located at the position L2 distant from the lower end of the V-shaped portion 13B, the auxiliary opening 20 is completely closed, as shown in FIG. 4(C). In other words, by providing the auxiliary opening 20 and increasing the operating range of the stop blade 15 by the distance L2, a gentle change in the quantity of light is realized.

As described above, when the opening angle of the V-shaped portion 13B is made small, a change in the quantity of light becomes gentle, but a loss of the quantity of light is caused in some region as compared with the case of a circular opening. The auxiliary opening 20 can compensate for the loss to a some extent. Although the auxiliary opening 20 is small in this embodiment, if it is made larger, it is possible to enhance the effect of compensating the loss of the quantity of light.

Figure 6:
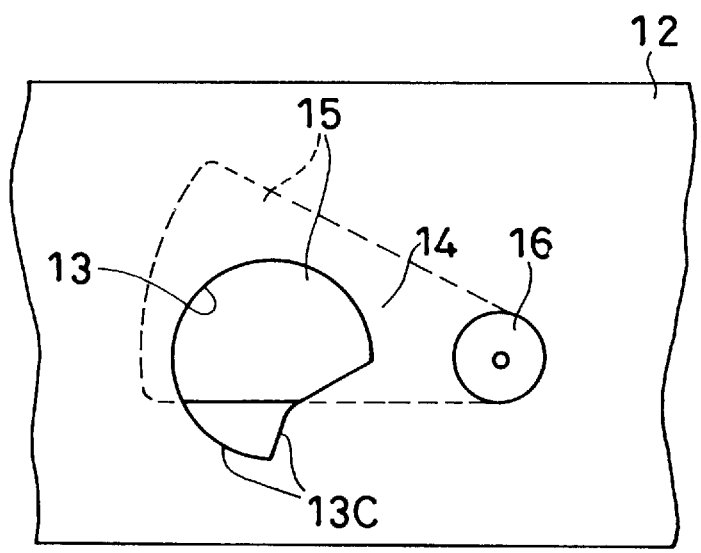
FIG. 6 shows another structure of the stop portion of the embodiment show in FIG. 1.

Although the noncircular opening 13 is composed of the arc portion and two V-shaped portions 13A and 13B in this embodiment, only one V-shaped portion or a curved V-shaped portion may be provided instead. Alternatively, one straight line of a V-shaped portion may be replaced by an arc, as represented by a noncircular portion 13C in FIG. 6. In addition, the auxiliary opening 20 may have a noncircular shape in place of a circular shape.

As explained above, since the noncircular opening which linearly changes the quantity of light from the light source is formed in the gate portion on which the stop blade is disposed, it is possible to stabilize the rate of change of the quantity of illuminating light with the quantity of movement of the stop blade especially in the region in which the aperture area of the opening is regulated to a small area, and it is possible to prevent the hunting phenomenon of the stop blade at the time of automatic light control.

In addition, since the auxiliary opening is formed in the single stop blade, it is possible to make a change in the quantity of illuminating light gentler, and a stabler controlling operation which is unlikely to produce the hunting phenomenon of the stop blade is realized. Furthermore, it is possible to compensate for the loss of the quantity of light due to the noncircular opening.

While there has been described what is at present considered to be a preferred embodiment of the invention, it will be understood that various modifications may be made thereto, and it is intended that the appended claims cover all such modifications as fall within the true spirit and scope of the invention.

What is claimed is:

1. A light source device for an endoscope comprising:

a gate portion including a noncircular opening for passing the light from a light source therethrough and linearly changing the quantity of light from said light source;

a stop blade for controlling the quantity of light passing through said noncircular opening of said gate portion; and a driving member for driving said stop blade, wherein said stop blade is a single blade with an auxiliary opening for passing part of light therethrough formed therein and said auxiliary opening is moved to a noncircular portion of said noncircular opening.

2. A light source device for an endoscope according to claim 1, wherein said noncircular opening is provided with a V-shaped portion.

* * * * *